(12) United States Patent
Hakki

(10) Patent No.: US 9,237,951 B1
(45) Date of Patent: Jan. 19, 2016

(54) APPARATUS AND METHOD FOR IDENTIFYING TIBIA BONE ROTATION IN KNEE IMPLANT SURGERY

(71) Applicant: Sam Hakki, St. Petersburg, FL (US)

(72) Inventor: Sam Hakki, St. Petersburg, FL (US)

(*) Notice: Subject to any disclaimer, the term of this patent is extended or adjusted under 35 U.S.C. 154(b) by 59 days.

(21) Appl. No.: 13/864,602

(22) Filed: Apr. 17, 2013

Related U.S. Application Data

(60) Provisional application No. 61/625,354, filed on Apr. 17, 2012.

(51) Int. Cl.
*A61F 2/38* (2006.01)
(52) U.S. Cl.
CPC ................................ *A61F 2/389* (2013.01)
(58) Field of Classification Search
CPC ...... A61F 2/389; A61F 2/3868; A61B 17/155
USPC .......... 623/16.11, 20.32–20.34; 606/86 R, 88
See application file for complete search history.

(56) References Cited

U.S. PATENT DOCUMENTS

| | | | |
|---|---|---|---|
| 6,385,475 B1 | 5/2002 | Cinquin et al. | |
| 6,514,259 B2 | 2/2003 | Picard et al. | |
| 6,692,447 B1 | 2/2004 | Picard et al. | |
| 6,915,150 B2 | 7/2005 | Cinquin et al. | |
| 6,923,817 B2 * | 8/2005 | Carson et al. | 606/130 |
| 7,033,360 B2 | 4/2006 | Cinquin et al. | |
| 8,603,093 B2 | 12/2013 | Hakki | |
| 2010/0076563 A1 * | 3/2010 | Otto et al. | 623/20.14 |

* cited by examiner

*Primary Examiner* — Jason-Dennis Stewart
(74) *Attorney, Agent, or Firm* — Frijouf, Rust & Pyle P.A

(57) ABSTRACT

A method and an apparatus are disclosed for identifying a proper tibia bone rotation relative to the femur bone for orientating a prosthesis in a knee replacement surgery. The proper tibia bone rotation is identified from an external rotation of the tibia in extension and an internal rotation of the tibia flexion. A point located midway between the external and internal rotations and a Whiteside line of the femur defines a center axis of tibia rotation plane. The rotational angles of the tibia may be measured by a mechanical goniometer or a computer navigation apparatus.

5 Claims, 5 Drawing Sheets

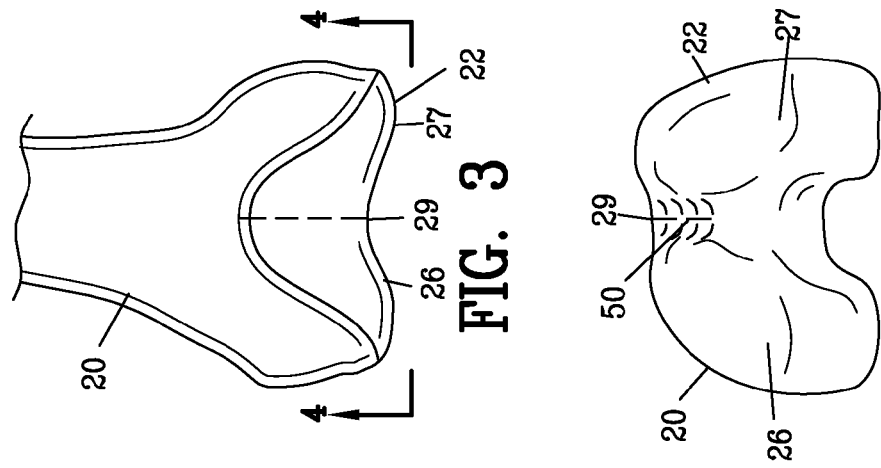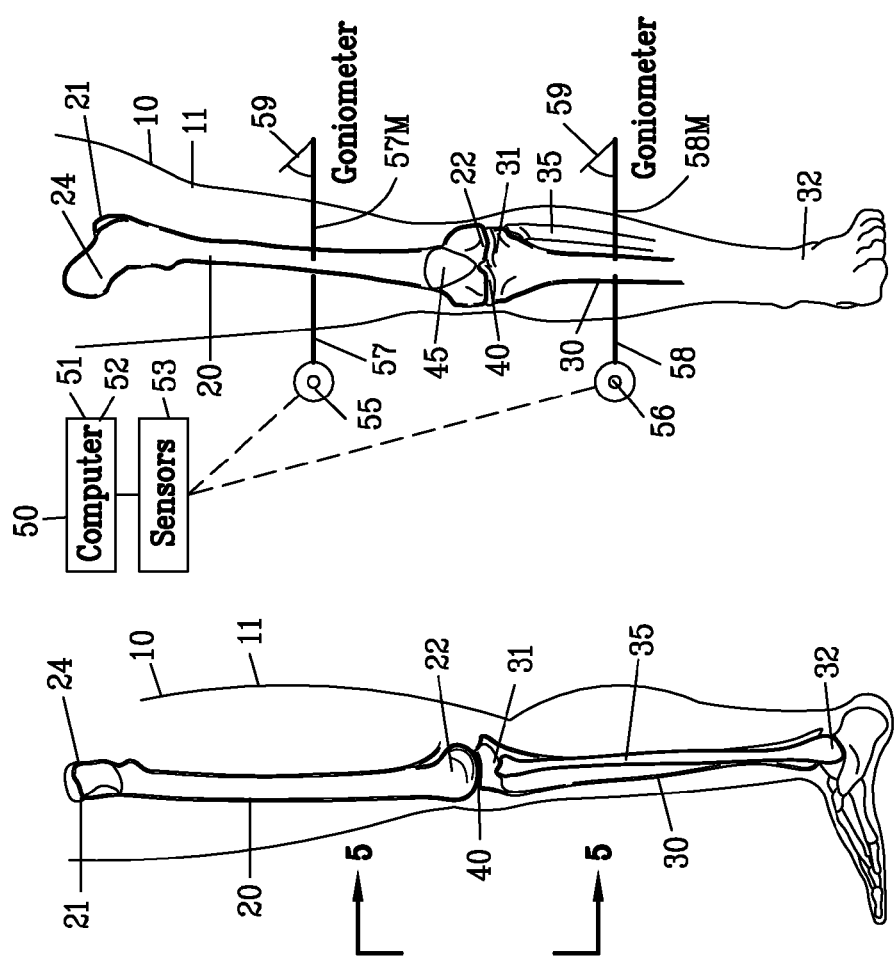

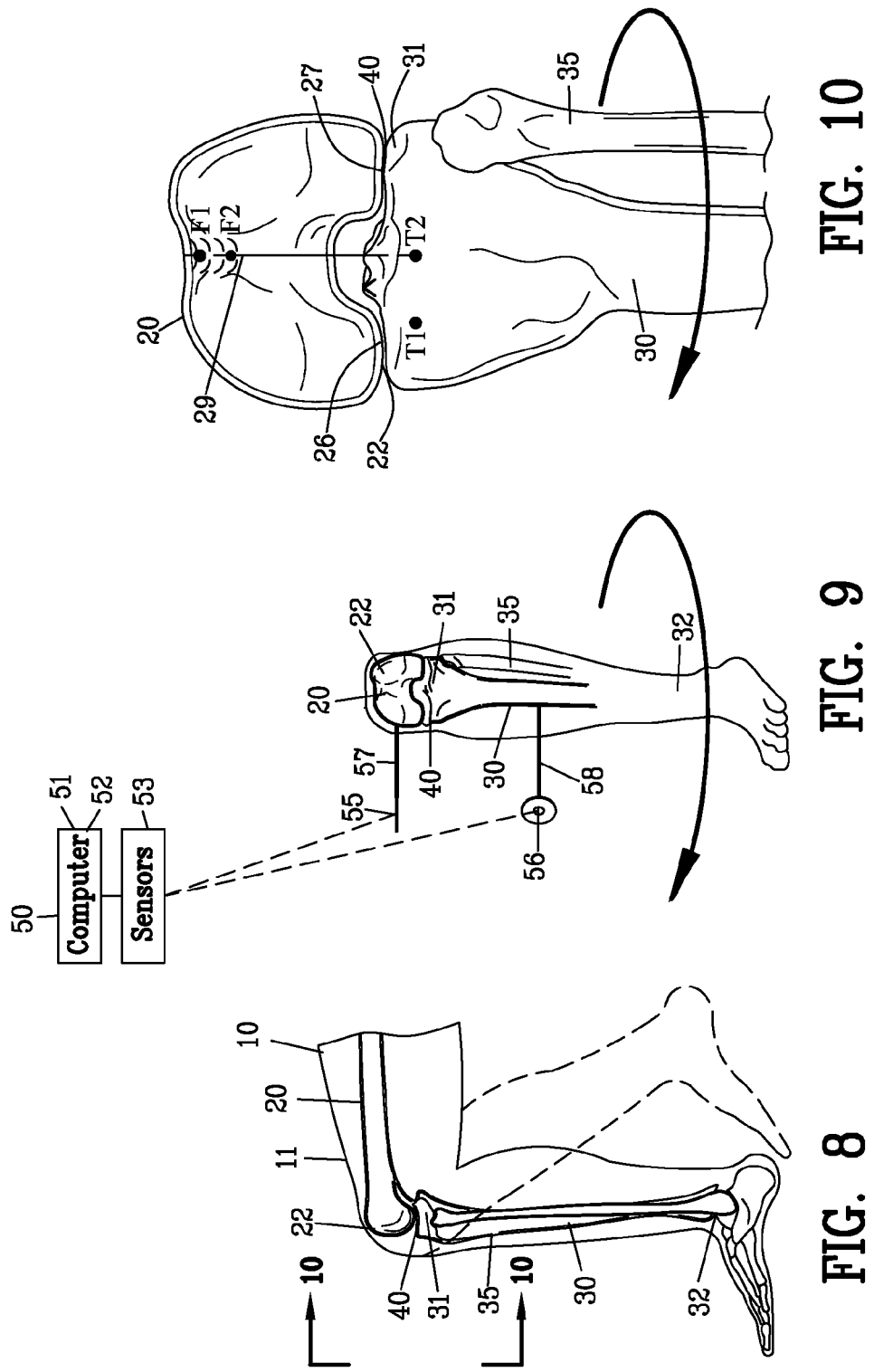

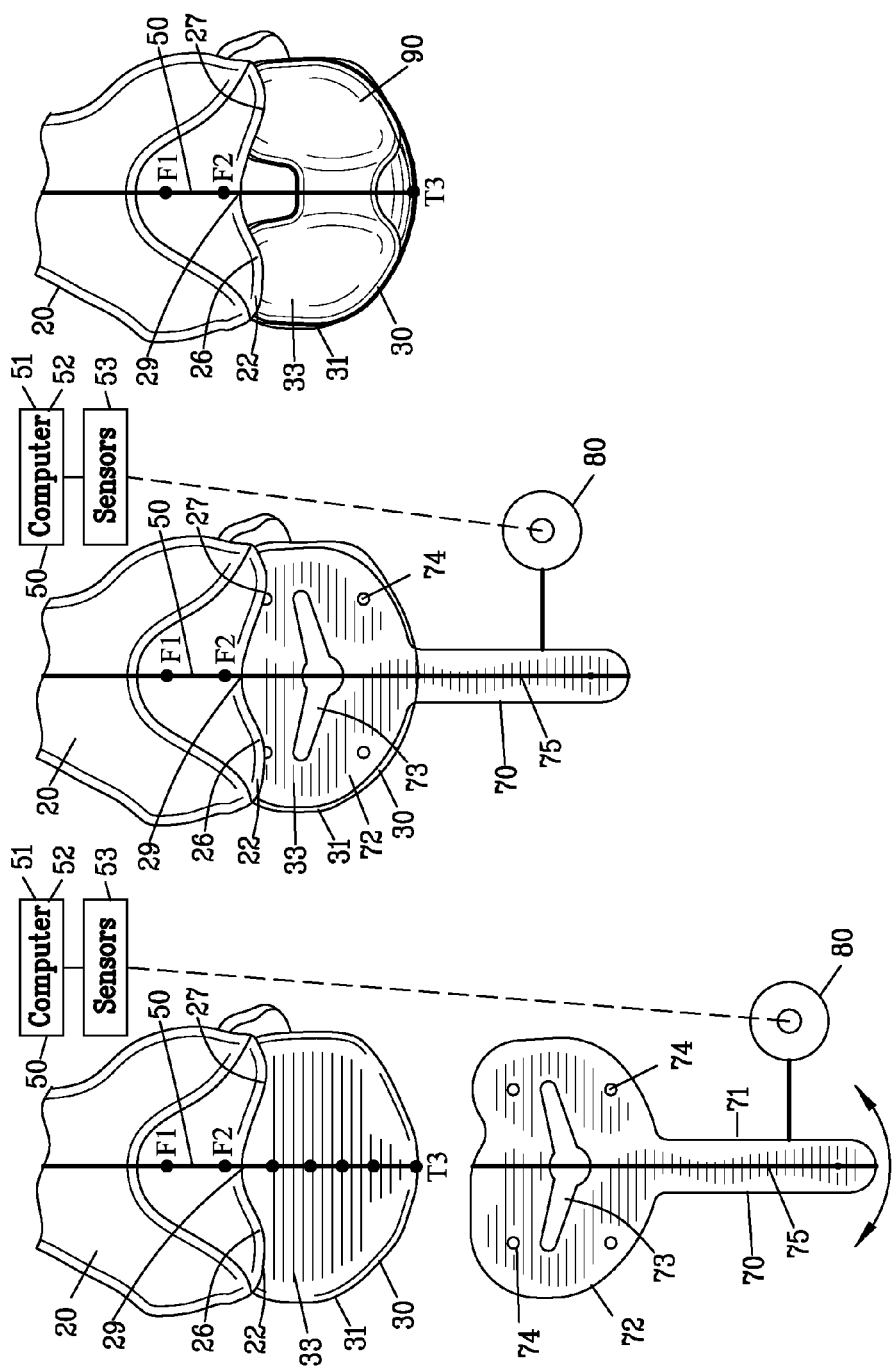

APPARATUS AND METHOD FOR IDENTIFYING TIBIA BONE ROTATION IN KNEE IMPLANT SURGERY

BACKGROUND OF THE INVENTION

1. Field of the Invention

This invention relates to surgery and more particularly to a method and an apparatus for identifying a proper tibia bone rotation relative to the femur bone in a knee replacement surgery.

2. Description of the Related Art

One of the most difficult measurements to be determined in a knee replacement surgery is the identification of the rotational angle of the tibia bone relative to the femur bone. Various types of measurements have been suggested by the prior art to determine the proper angular rotation between the tibia bone relative to the femur bone. Many computer programs have been developed to assist in the identification of the rotational angle of the tibia bone relative to the femur bone. The following United States Patents are representative of computer programs developed for orthopedic surgery.

U.S. Pat. No. 6,385,475 to Cinquin, et al discloses a process for the preoperative determination of the positioning data of endoprosthetic parts of a central joint relative to the bones forming the central joint, a respective outer articular point is determined by way of movement of the bones about a respective outer joint which is located at the end of the two bones facing away from the central joint. An articular point is determined for each of the two bones in the area of the central joint, and a direction characteristic for each of these bones is determined by way of a straight-line connection of the two articular points obtained in this manner for the two bones. The orientation of the endoprosthetic parts relative to this characteristic direction is then determined. Apparatus for carrying out the process is also provided.

U.S. Pat. No. 6,514,259 to Picard, et al, discloses a plate probe and associated system and method for facilitating the orientation of an osteotomy and the implantation of an artificial joint component during arthroplastic surgery requiring an osteotomy. The probe comprises a coupler and a plate. The coupler is configured so that it can be connected to a position tracker, such that the position and orientation of the plate can be determined from the position of the tracker. The plate is configured so that it can be inserted into an opening of a bone-cutting mechanical guide, which is generally designed for receiving and guiding a surgical saw blade during a cutting operation.

U.S. Pat. No. 6,692,447 to Picard discloses a system for determining pivot centers for proximal and intermediary articulations of an appendicular skeleton. The system includes a single marker affixed to a bone, the marker having a signal transmitter; a sequence involving at least one movement for moving a portion of the appendicular skeleton; a signal receiver for collecting data points correlating to the position and orientation of the marker; at least one processing device for selecting a number of skeletal positions during, the sequence using the collected data points; and for assigning a value to each posture representing the position and orientation of the marker in a predetermined point of reference, and an algorithm for determining the coordinates of the rotational centers of the proximal and intermediary articulations using the assigned values.

U.S. Pat. No. 6,915,150 to Cinquin, et al. discloses a process for the preoperative determination of the positioning data of endoprosthetic parts of a central joint relative to the bones forming the central joint, a respective outer articular point is determined by way of movement of the bones about a respective outer joint which is located at the end of the two bones facing away from the central joint. An articular point is determined for each of the two bones in the area of the central joint, and a direction characteristic for each of these bones is determined by way of a straight-line connection of the two articular points obtained in this manner for the two bones. The orientation of the endoprosthetic parts relative to this characteristic direction is then determined. Apparatus for carrying out the process is also provided.

U.S. Pat. No. 7,033,360 to Cinquin, et al. discloses a process for the preoperative determination of the positioning data of endoprosthetic parts of a central joint relative to the bones forming the central joint, a respective outer articular point is determined by way or movement of the bones about a respective outer joint which is located at the end of the two bones facing away from the central joint. An articular point is determined for each of the two bones in the area of the central joint, and a direction characteristic for each of these bones is determined by way of a straight-line connection of the two articular points obtained in this manner for the two bones. The orientation of the endoprosthetic parts relative to this characteristic direction is then determined. Apparatus for carrying out the process is also provided.

Although many computer programs have been developed to assist in the identification of the rotational angle of the tibia bone relative to the femur bone, the identification of the proper rotational angle of the tibia bone still eludes the medical art.

Identification of tibia rotation in a knee replacement is very difficult. Some surgeons rely on relation to tibia tuberosity that proved to be unreliable. Other surgeons rely on tibia rotation established by previous knee replacement surgeons and that proved to be unreliable. Presently, there is no scientific accurate way of identifying the knee tibia rotation in knee surgery.

The reason is the tibia has a wide range of rotation especially after transecting the proximal 10 mm or so as a routine step in knee replacement. It is difficult to choose the right spot on the tibia and consider that to be the ideal tibia rotation.

Therefore, it is an object of the present invention to provide a method for determining the proper rotational angle between a tibia bone relative to a femur bone in a knee replacement surgery.

Another object of the invention is to provide a method for determining the proper rotational angle between a tibia, bone relative to a femur bone which is determined by the physical properties of the patient.

Another object of the invention is to provide a method for determining the proper rotational angle between a tibia bone relative to a femur bone which is determined by an external rotation of the tibia in extension and an internal rotation of the tibia flexion.

Another object of the invention is to provide an apparatus for determining the proper rotational angle between a tibia bone relative to a femur bone comprising computer hardware and computer software incorporating the present method.

The foregoing has outlined some of the more pertinent objects of the present invention. These objects should be construed as being merely illustrative of some of the more prominent features and applications of the invention. Many other beneficial results can be obtained by applying the disclosed invention in a different manner or modifying the invention with in the scope of the invention. Accordingly other objects in a full understanding of the invention may be had by referring to the summary of the invention and the detailed description describing the preferred embodiment of the invention.

SUMMARY OF THE INVENTION

A specific embodiment of the present invention is shown in the attached drawings. For the purpose of summarizing the invention, the invention relates to an improved method for identifying a proper tibia bone rotation relative to the femur bone for orientating a prosthesis in a knee replacement surgery. The method comprises the step of externally rotating the tibia relative to the femur when the tibia is in extension. The tibia is internally rotated relative to the femur when the tibia is in flexion. The proper tibia bone rotation relative to the femur bone is identified from the limits established by the external and internal tibia rotation. The prosthesis is aligned onto the tibia in accordance with the identified proper tibia bone rotation.

In another example of the invention, the method comprises marking a first point T1 on the tibia corresponding to an external rotation of the tibia when the tibia is in extension. A second point T2 is marked on the tibia corresponding to an internal rotation of the tibia when the tibia is in flexion. A third point T3 is marked on the tibia midway between the first point T1 and the second point T2. A center axis of tibia rotation plane is determined by the third point T3 and a groove defined by a deepest part of a distal end of a femur between a medial and a lateral condyles. The prosthesis is aligned onto the tibia in accordance with the center axis of tibia rotation plane.

In a more specific example, the step of marking the first, second and third points on the tibia include marking the first, second and third points on the tibia with a computer navigation system. In an alternate example, the step of marking the first, second and third points on the tibia include marking the first, second and third points on the tibia with a mechanical goniometer. Preferably, the step of aligning the prosthesis onto the tibia includes aligning an axis of a template in accordance with the with the center axis of tibia rotation plane.

In a more specific embodiment, the method comprises the steps of marking a Whiteside line on the distal end of the femur. The tibia is orientated in extension relative to the femur. The tibia is externally rotated relative to the femur while the tibia is in full extension. A first point T1 is marked on the tibia corresponding to the location of the Whiteside line. The tibia is oriented in flexion relative to the femur. The tibia is internally rotated relative to the femur while the tibia is in flexion. A second point T2 is marked on the tibia corresponding to the location of the Whiteside line. A third point T3 is marked on the tibia midway between the first point T1 and the second point T2. A center axis of tibia rotation plane is determined by the third point T3 and the Whiteside line. The prosthesis is aligned onto the tibia in accordance with the center axis of tibia rotation plane.

The invention is also incorporated into an apparatus for identifying a proper tibia rotation relative to the femur for orientating a prosthesis in a knee replacement surgery. The apparatus comprises a computer having a display. A plurality of navigation sensors are connected to the computer. A first position tracker is secured to a femur of a patient. A second position tracker secured to a tibia of the patient. The computer marks a Whiteside line located on the distal end of the femur. The computer marks an externally rotating tibia relative to the femur when the tibia is in extension. The computer marks an internally rotated tibia relative to the femur when the tibia is in flexion. The computer determines a center axis of tibia rotation plane determined by the external and internal rotation of the tibia relative to the femur and the Whiteside line. A third position tracker is secured to a template. An axis of the template is aligned in accordance with the with the center axis of tibia rotation plane.

The foregoing has outlined rather broadly the more pertinent and important features of the present invention in order that the detailed description that follows may be better understood so that the present contribution to the art can be more fully appreciated. Additional features of the invention will be described hereinafter which form the subject matter of the invention. It should be appreciated by those skilled in the an that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention.

BRIEF DESCRIPTION OF THE DRAWINGS

For a fuller understanding of the nature and objects of the invention, reference should be made to the following detailed description taken in connection with the accompanying drawings in which:

FIG. 1 is a side view of a left leg of a patient illustrating the femur bone and the tibia bone;

FIG. 2 is a front view of a left leg of the patient illustrating positional sensors secured to the femur bone and the tibia bone;

FIG. 3 is an enlarged front view of a distal end of a left femur illustrating Whiteside line located between the medial and lateral condyles;

FIG. 4 is a view along line 4-4 in FIG. 3;

FIG. 8 is a side view of the left leg of the patient in flexion;

FIG. 9 is a front view of the left leg of the patient in flexion with the tibia being internally rotation relative to the femur;

FIG. 10 is a magnified view a portion of FIG. 9 illustrating the marking a second point T2 on the tibia corresponding to the location of the Whiteside line;

FIG. 14 illustrates the alignment of a template probe in accordance with the center axis of tibia rotation plane;

FIG. 15 illustrates a movement of the template probe into proper position on the tibia; and FIG. 16 illustrates the mounting of the tibia prosthesis on the proximal end of the tibia bone.

Similar reference characters refer to similar parts throughout the several Figures of the drawings.

DETAILED DISCUSSION

Figure 7:
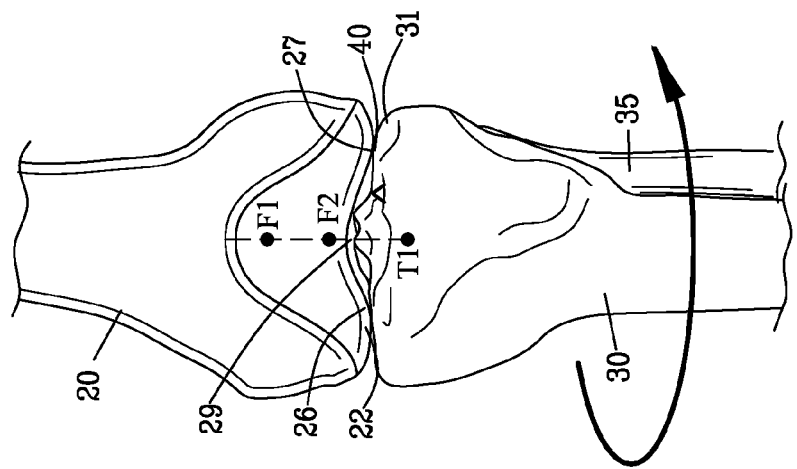
FIG. 7 is a magnified view a portion of FIG. 6 illustrating the marking a first point T1 on the tibia corresponding to the location of the Whiteside line.

FIGS. 1 and 2 are side view (lateral view) and a front view (anteroposterior view) of a left leg 10 of a patient 11. A femur 20 extends from a proximal end 21 to a distil end 22. The proximal end 21 of the femur 20 includes a femoral head 24. A tibia 30 extends from a proximal end 31 to a distal end 32. A fibula is disposed on a lateral side of the tibia 30. A fibula 35 is located adjacent to the tibula 20.

The distal end 22 of the femur 20 is located adjacent to the proximal end 31 of the tibia 30 forming a femorotibial joint 40. The femorotibial joint 40 provides articulation between the femur 20 and the tibia 30. A patella 45 is shown located adjacent to the distal end 22 of the femur 20. It should be appreciated that by those skilled in the medical art that the drawings have been simplified for the sake of clarity in setting forth the present invention.

In many cases, the surface of the distal end 22 of the femur 20 and/or the surface of the proximal end 31 of the tibia 30 are damaged by injury, disease and the like. The damage to the distal end 22 to the femur 20 and/or the proximal end 31 of the tibia 30 results in a painful articulation between the femur 20 and the tibia 30 for the patient 11.

The present invention provides a method for identifying the proper tibia bone 30 rotation relative to the femur bone 20 in a knee replacement surgery.

There are many types of computer and mechanical systems of implementing the process of the present invention. The present invention may be incorporated into an apparatus including a computer and software program for use with the computerized navigation systems such as the computer navigation systems set forth in U.S. Pat. Nos. 6,385,475, 6,514, 259, 6,692,447, 6,915,150 and 7,033,360 that are incorporated by reference into the present specification.

A computer navigation systems 50 comprises a computer 51 with appropriate computer software 52 connected to a plurality of receivers 53. Preferably, the plurality of receivers 53 are located at various locations throughout an operating room (not shown).

Transmitters 55 and 56 are secured to the femur 20 and to the tibia 30 by bone screws 57 and 58. Each of the plurality of receivers 53 are arranged in spaced relation to one another enabling the computer to determine the position and the orientation of the femur 20 and the tibia 30 by the transit-time differences between the each of the Transmitters 55 and 56 and each of the plurality of receivers 53.

In the alternative, the method of the present invention may be implemented with the use of traditional mechanical devices. Bone screws 57M and 58M are secured to the femur 20 and to the tibia 30. A mechanical goniometer 59 is used to measure the rotational angle between the bone screws 57M and 58M to determine the angle between the femur 20 and the tibia 30.

FIGS. 3 and 4 are enlarged views of the distal end 22 of the femur bone 20. The distal end 22 of the femur bone 20 terminates in a medial condyle 26 and a lateral condyle 27. A Whiteside line 29 is defined by a deepest part of the distal end 22 of the femur 20 between the medial condyle 26 and the lateral condyle 27. The Whiteside line 29 commonly referred to as a patella groove is a groove wherein the patella 40 slides down in flexion. The details of the anatomy of the femur 20, the tibia 30 and the patella 40 as well as the details of a total knee replacement surgery should be well known by those skilled in the medical art.

Figure 5:
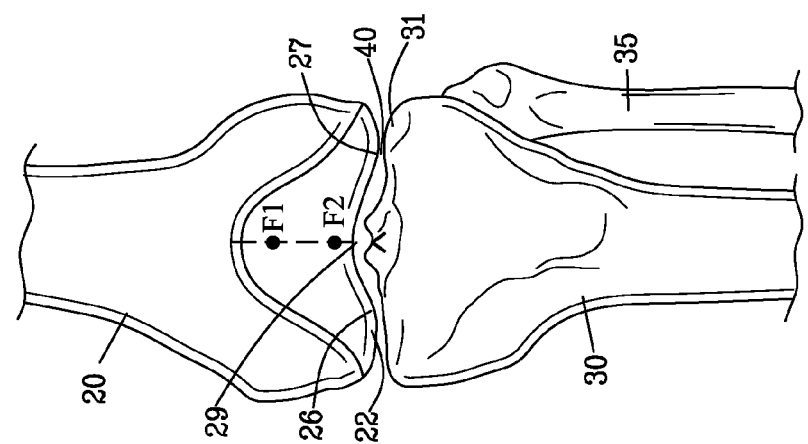
FIG. 5 is a magnified view a portion of FIG. 4 illustrating a marking a Whiteside line of the femur between the medial and lateral condyles.

FIG. 5 is a magnified view a portion of FIG. 4 illustrating a process step of marking the Whiteside line 29 of the femur 20 located between the medial condyle 25 and the lateral condyle 27 of the distal end 22 of the femur 20. The Whiteside line 29 is marked by points F1 and F2 to externally identify the Whiteside line 29. The marked of points F1 and F2 may be either a marking by the computer navigation systems 50 or may be by physically marking the distal end 22 of the femur 20 by a marker pen (not shown). The symbol ^on the proximal end of the tibia 30 is for the purpose of illustrating the process of the present invention.

Figure 6:
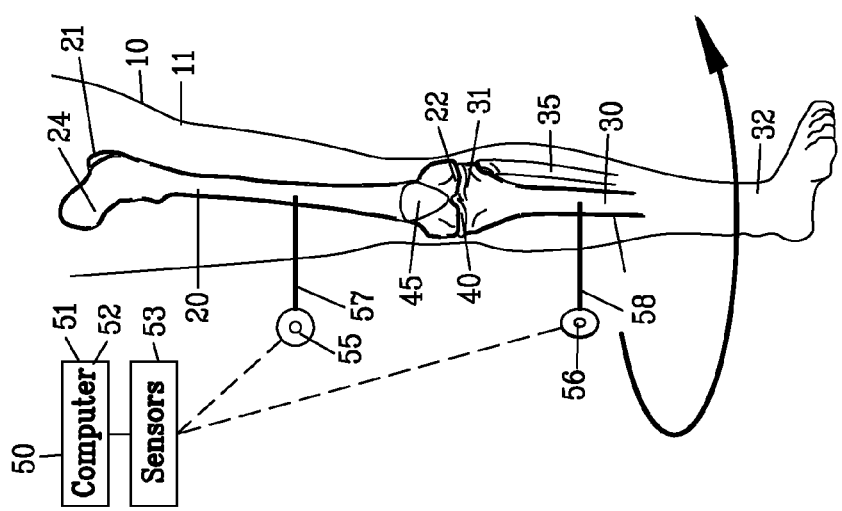
FIG. 6 is a front view of the left leg of the patient in full extension with the tibia being in external rotation relative to the femur.

FIG. 6 is a front view of the left leg 10 of the patient 11 in full extension with the tibia 30 being externally rotated relative to the femur 20. The tibia bone 30 is externally rotated relative to the femur bone 20 as indicated by the arrow to an extreme external rotation. The extreme external rotation of the tibia bone 30 relative to the femur bone 20 is limited by the physical properties of the specific patient 11 including the knee ligaments (not shown).

FIG. 7 is a magnified view a portion of FIG. 6 illustrating the marking a first point T1 on the tibia 30 corresponding to the location of the Whiteside line 29. The marking of the first point T1 on the proximal end 31 of the tibia 30 may be either a marking by the computer navigation systems 50 or may be by physically marking the proximal end 31 of the tibia 30.

FIG. 8 is a side view of the left leg 10 of the patient 11 with the tibia 30 in full flexion relative to the femur 20. Typically, the tibia 30 can be flexed between seventy degrees (70°) to one hundred and ten degrees (110°) in full flexion depending on the physical attributes of the patient 11.

When the tibia 30 in flexion relative to the femur 20 as shown in FIG. 8, the tibia 30 may be internally rotated relative to the femur 20 to a greater rotation angle than when the tibia 30 is internally rotated when the tibia 30 is in extension as shown in FIG. 6. The difference of the extreme internal rotation when the tibia 30 is in extension as shown in FIG. 6 and when the tibia 30 is in flexion is a physical property of the femorotibial joint 40 including the knee ligaments (not shown).

FIG. 9 is a front of the left leg 10 of the patient 11 in full flexion with the tibia 30 being internally rotated relative to the femur 20. The tibia bone 30 is internally rotated relative to the femur bone 20 as indicated by the arrow to an extreme internal rotation. The extreme internal rotation of the tibia bone 30 relative to the femur bone 20 is limited by the physical properties of the specific patient 11 including the knee ligaments (not shown).

FIG. 10 is a magnified view a portion of FIG. 9 illustrating the marking a second point T2 on the tibia 30 corresponding to the location of the Whiteside line 29. The marking of the second point T2 on the proximal end 31 of the tibia 30 may be either a marking by the computer navigation systems 50 or may be by physically marking the proximal end 31 of the tibia 30.

Figure 12:
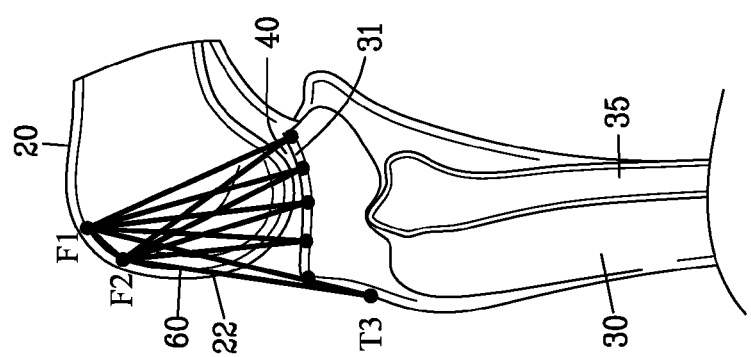
FIG. 12 is a side view of the left leg of the patient in flexion on illustrating the defining of a center axis of tibia rotation plane determined by the third point T3 and the Whiteside line.
Figure 11:
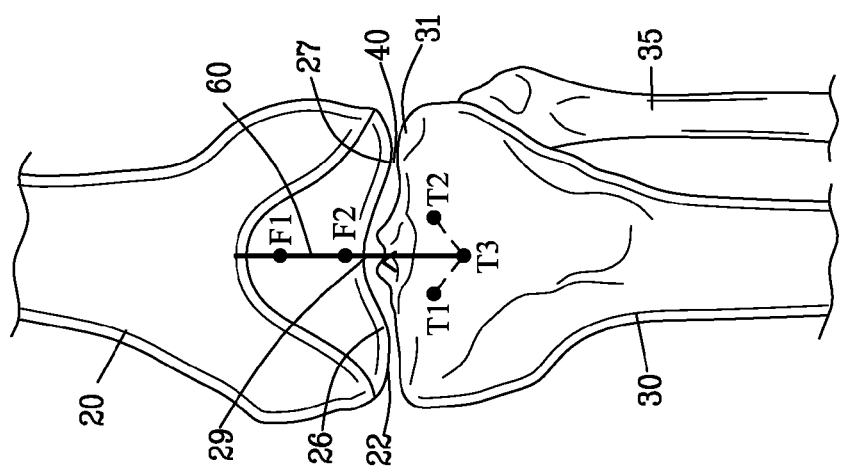
FIG. 11 is a view similar to FIG. 10 illustrating the marking a third point T3 on the tibia midway between the first point T1 and the second point T2.

FIGS. 11 and 12 are front and side views of the left leg 10 of the patient 11 illustrating the marking a third point T3 on the proximal end 31 of the tibia 30. The third point T3 on the proximal end 31 of the tibia 30 is midway between the first point T1 and the second point T2. The marking of the third point T3 on the proximal end 31 of the tibia 30 may be either a marking by the computer navigation systems 50 or may be by physically marking the proximal end 31 of the tibia 30.

It is well known in geometry that two points define a line. An infinite number of planes extend through the two points defining the line. It is also well known in geometry that three non-colinear points uniquely define a plane.

The whiteside line 29 defines an infinite number of planes extending through the marked points F1 and F2. The marked points F1 and F2 of the Whiteside line 29 in combination with the third point T3 define a central plane of tibia rotation 60. The true center axis of the rotation of the tibia is contained within the central plane of tibia rotation 60. The central plane of tibia rotation 60 is in both the sagittal and the frontal (coronal) planes.

Figure 13:
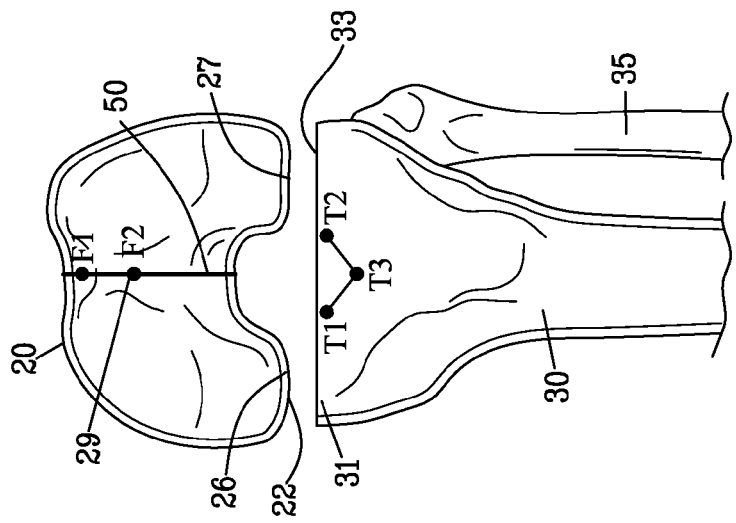
FIG. 13 is a view similar to FIG. 11 illustrating a severed proximal end of the tibia.

FIG. 13 is a view similar to FIG. 11 illustrating a severed proximal end 31 of the tibia 30. The proximal end 31 of the tibia 30 is shown severed to define a severed proximal end 33. The severing of the proximal end 31 of the tibia 30 removes the damaged surface of the surface of the proximal end 31 of the tibia 30. The severing of the proximal end 31 of the tibia 30 results in a loss of an identification of the proper rotational angle of the tibia bone 30 relative to the femur bone 20.

FIG. 14 illustrates the alignment of a probe template 70 positioned adjacent to the severed the proximal end 31 of the tibia 30. The probe template 70 comprises a handle 71 supporting a template 72 having a tibial stem hole 73 and a tibial mounting hole 74. The template 72 is symmetrically disposed about a template axis 75.

A position tracker transmitter 80 is affixed to the handle 71 of the probe template 70. The position tracker transmitter 80 enables the computer system to align the template axis 75 in accordance with the central plane of tibia rotation 60. In the alternative, the probe template 70 may be aligned in accordance with the physically marked the proximal end 31 of the tibia 30. As long as the template axis 75 of the probe template 70 aligned with the central plane of tibia rotation 60, the probe template 70 is positioned with the proper angular rotation of the tibia 30.

FIG. 15 illustrates a movement of the template probe 70 into proper position on the severed proximal end 33 of the tibia 30. The template axis 75 of the template probe 70 is positioned in accordance with the central plane of tibia rotation 60. In the alternative, the probe template 70 may be aligned in accordance with the physically marked the proximal end 31 of the tibia 30.

The template 72 of the probe template 70 is oriented on the severed proximal end 33 in an anterior/posterior direction by the surgeon. The alignment of the probe template 70 with the central plane of tibia rotation 60 insures the surgeon does not change the rotation of the probe template 70 during the process of inserting the template 72 on the severed proximal end 33. A change in the rotation of the probe template 70 during the process of the template 72 is a of common mistake in mal rotated tibia implants. This common mistake is caused in part by the shape of the severed proximal end 33 of the tibia 30 being non-circular since the medial condyle 26 is always larger that the lateral condyle 27. The non-circular severed proximal end 33 of the tibia 30 makes orientation the template 72 more difficult tempting a surgeon to push the template 72 more medial due to the patella tendon and more mal rotated internally due to the naturally more internal rotation of the tibia 30 that takes place with more flexion. Preferably, the probe template 70 is positioned on the severed proximal end 33 to expose a portion of the tibia 30 about the probe template 70.

After the template probe 70 is properly positioned on the severed proximal end 33 of the tibia 30, a tibial stem hole 73 is formed in the severed proximal end 33 of the tibia bone 30. Tibial mounting holes 87 made be used to temporally affix the template probe 70 on the severed proximal end 33 of the tibia 30 during the forming of the tibial stem hole 73.

FIG. 16 illustrates the mounting of the tibia prosthesis 90 on the severed proximal end 33 of the tibia bone 30. The tibia prosthesis 90 is secured to the severed proximal end 33 of the tibia bone 30 in a conventional manner as should be well known to those skilled in the art.

The present invention provides a method for determining the proper rotational angle between a tibia bone relative to a femur bone in a total knee arthroplasty (TKA). The method for determines the proper rotational angle between a tibia relative to a femur in accordance with the physical properties of the patient. The method results in the maximum range of motion (ROM) of the femorotibial joint in accordance with the physical properties of the specific patient.

Although the invention has been described in its preferred form with a certain degree of particularity, it is understood that the present disclosure of the preferred form has been made only by way of example and that numerous changes in the details of construction and the combination and arrangement of pans may be resorted to without departing from the spirit and scope of the invention.

What is claimed is:

1. The method for identifying a proper tibia bone rotation relative to the femur bone for orientating a prosthesis in a knee replacement surgery comprising the step of:
   marking a first point T1 on the tibia corresponding to an external rotation of the tibia when the tibia is in extension;
   marking a second point T2 on the tibia corresponding to an internal rotation of the tibia when the tibia is in flexion;
   marking a third point T3 on the tibia midway between the first point T1 and the second point T2;
   defining a center axis of tibia rotation plane determined by the third point T3 and a groove defined by a deepest part of a distal end of a femur between a medial and a lateral condyles; and
   aligning the prosthesis onto the tibia in accordance with the center axis of tibia rotation plane.

2. The method for identifying a proper tibia bone rotation relative to the femur bone as set forth in claim 1, wherein the step of marking the first, second and third points on the tibia include marking the first, second and third points on the tibia with a computer navigation system.

3. The method for identifying a proper tibia bone rotation relative to the femur bone as set forth in claim 1, wherein the step of marking the first, second and third points on the tibia include marking the first, second and third points on the tibia with a mechanical goniometer.

4. The method for identifying a proper tibia hone rotation relative to the femur bone as set forth in claim 1, wherein the step of aligning the prosthesis onto the tibia includes aligning an axis of a template in accordance with the with the center axis of tibia rotation plane.

5. The method for identifying a proper tibia bone rotation relative to the femur bone for orientating a prosthesis in a knee replacement surgery comprising the step of:
   marking the Whit side line of the femur;
   orientating the tibia in extension relative to the femur;
   externally rotating the tibia relative to the femur while the tibia is in full extension;
   marking a first point T1 on the tibia corresponding to the location of the Whiteside line;
   orientating the tibia in flexion relative to the femur;
   internally rotating the tibia relative to the femur while the tibia is in flexion;
   marking, a second point T2 on the tibia corresponding to the location of the Whiteside line;
   marking a third point T3 on the tibia midway between the first point T1 and the second point T2;
   defining a center axis of tibia rotation plane determined by the third point T3 and the Whiteside line; and
   aligning the prosthesis onto the tibia in accordance with the center axis of tibia rotation plane.

\* \* \* \* \*